United States Patent [19]
Kuestner

[11] Patent Number: 5,377,674
[45] Date of Patent: Jan. 3, 1995

[54] METHOD FOR NON-INVASIVE AND IN-VITRO HEMOGLOBIN CONCENTRATION MEASUREMENT

[76] Inventor: J. Todd Kuestner, 26 Wild Duck Rd., Wyckoff, N.J. 07481

[21] Appl. No.: 181,635

[22] Filed: Jan. 13, 1994

Related U.S. Application Data

[63] Continuation-in-part of Ser. No. 4,404, Jan. 14, 1993, abandoned, which is a continuation-in-part of Ser. No. 965,817, Oct. 23, 1992, abandoned, which is a continuation-in-part of Ser. No. 880,379, May 8, 1992, abandoned.

[51] Int. Cl.$^6$ ............................................. A61B 5/00
[52] U.S. Cl. .................................... 128/633; 128/664; 128/665; 128/666; 356/41
[58] Field of Search ............................... 128/633–634, 128/664–667; 356/30–41

[56] References Cited

U.S. PATENT DOCUMENTS

| | | | |
|---|---|---|---|
| 5,070,874 | 12/1991 | Barnes et al. | 128/664 X |
| 5,127,406 | 7/1992 | Yamaguchi | 128/633 |
| 5,137,023 | 8/1992 | Mendelson | 128/633 |
| 5,183,042 | 2/1993 | Harjunmaa et al. | 128/633 |
| 5,204,532 | 4/1993 | Rosenthal | 128/633 X |

*Primary Examiner*—Angela D. Sykes
*Attorney, Agent, or Firm*—Kenyon & Kenyon

[57] ABSTRACT

A non-invasive and an in-vitro method for determining a person's hemoglobin concentration are described. The methods employ substantially simultaneous measurements of absorbance of near-infrared and long wavelength visible light. The measurement consists of a combination of ordinary absorbance data at multiple wavelengths in the form of a ratio or of a ratio of derivative absorbance data. The method minimizes the need for path-length measurement or extinction coefficient determination or estimation of scattering losses. In the in-vitro setting, the method minimizes the need for cell lysis or for reagents.

11 Claims, 10 Drawing Sheets

FIG.1 λ/ε CURVE OF OXYHAEMOGLOBIN (HbO₂)

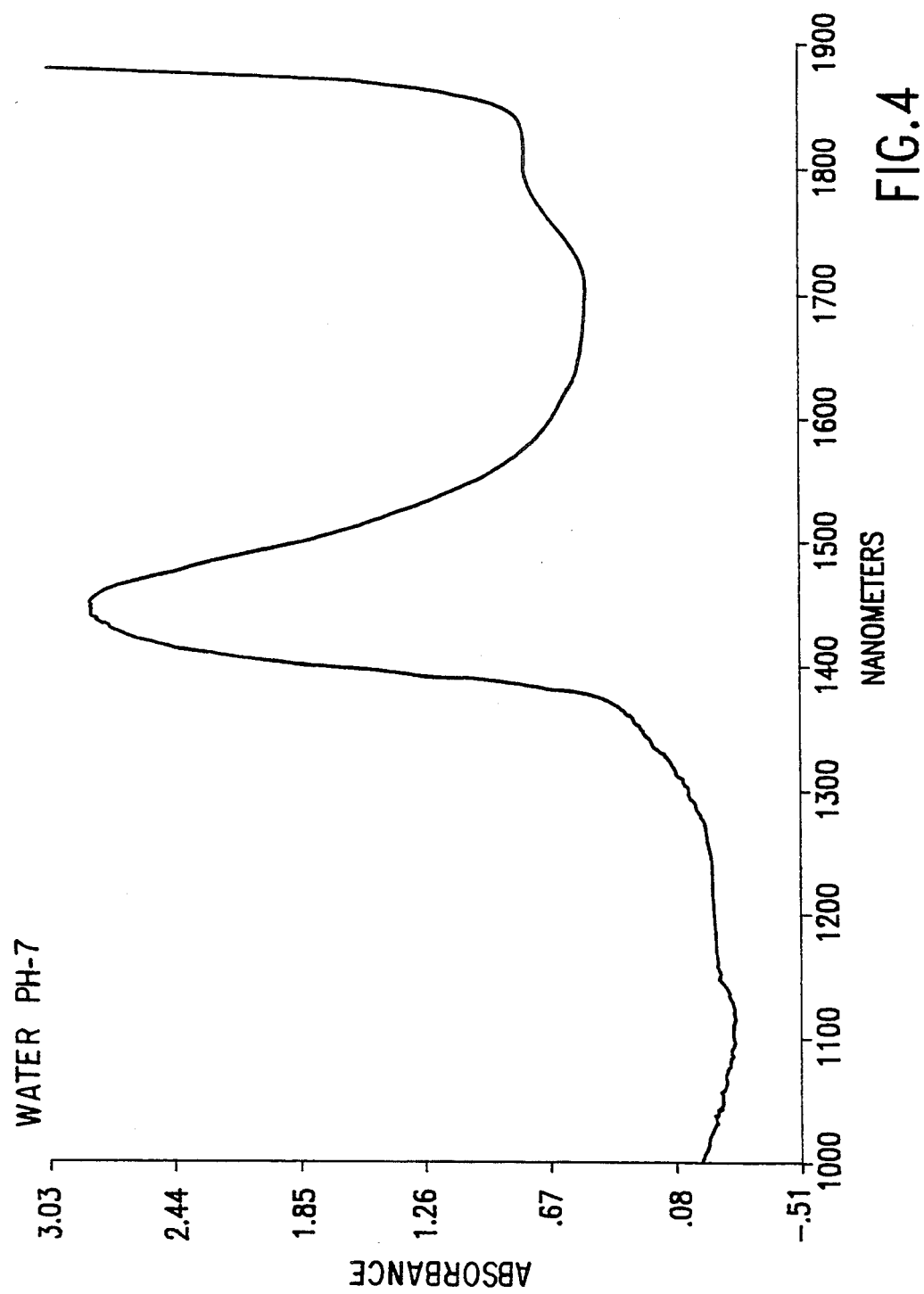

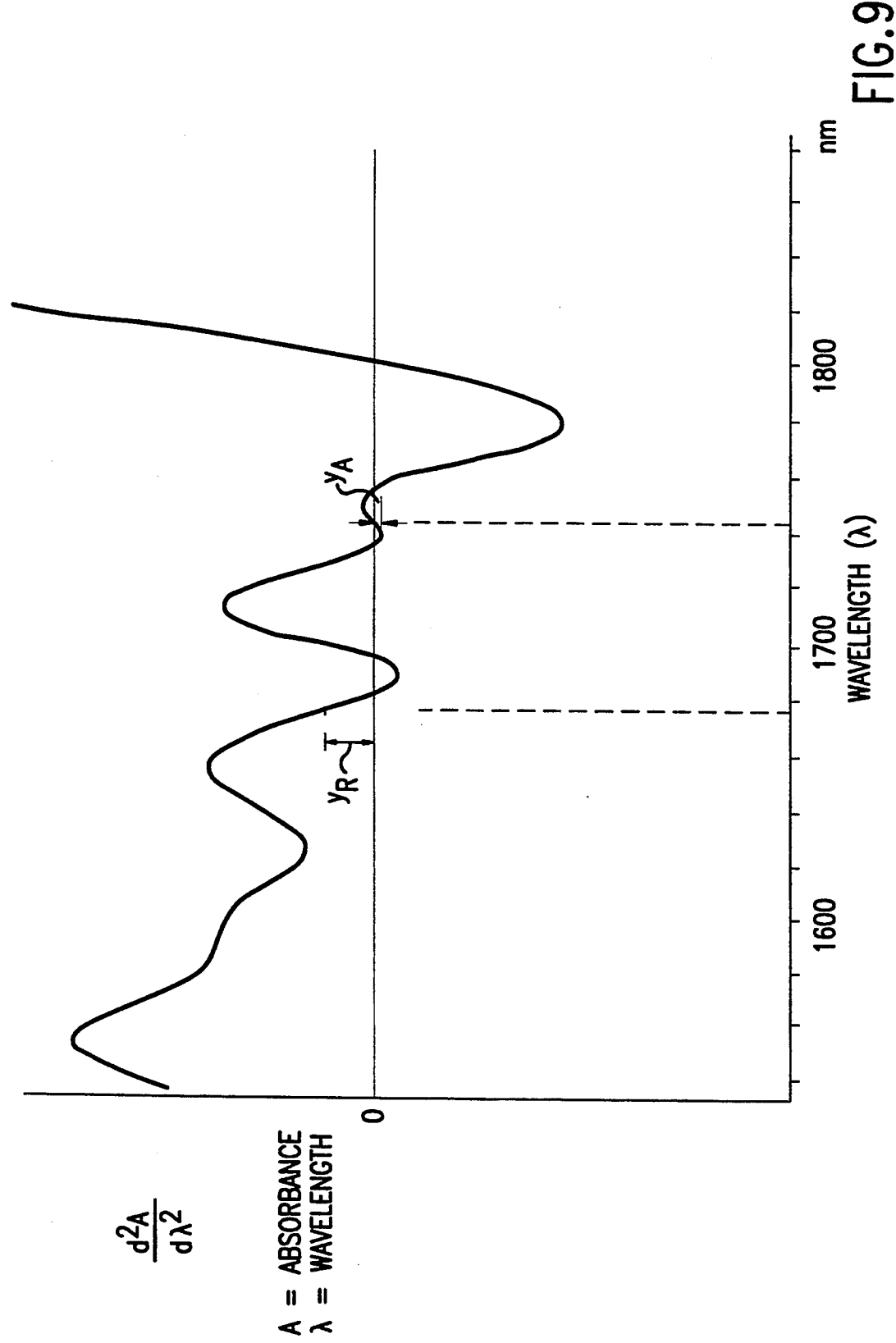

METHOD FOR NON-INVASIVE AND IN-VITRO HEMOGLOBIN CONCENTRATION MEASUREMENT

This application is a continuation-in-part of U.S. patent application Ser. No. 08/004,404 filed Jan. 14, 1993, now abandoned. It is in turn a continuation-in-part of U.S. patent application Ser. No. 07/965,817, filed Oct. 23, 1992 now abandoned, which is a continuation-in-part of U.S. patent application Ser. No. 07/880,379, filed May 8, 1992, now abandoned, a continuation of which was filed Sept. 24, 1993 and assigned Ser. No. 08/126,024.

FIELD OF THE INVENTION

The present invention relates to a non-invasive method for determining hemoglobin concentration in tissue and to an in-vitro method for determining hemoglobin concentration in blood.

BACKGROUND

Methods and devices for non-invasively determining the percentage of hemoglobin which is carrying oxygen are generally known in the medical field. This percentage is referred to as hemoglobin saturation. The type of hemoglobin which carries oxygen is called oxyhemoglobin, while the type of hemoglobin which is devoid of oxygen is called deoxyhemoglobin. Hemoglobin saturation is of interest since it indicates the degree of oxygenation of the blood in the tissues.

A device which can perform a non-invasive measurement of hemoglobin saturation is generally referred to as a pulse oximeter. With this device, light is transmitted through a monitoring site which is usually the finger, ear or toe. The pulse oximeter measures absorbances in the visible and near-infrared ranges of the electromagnetic spectrum, in order to measure hemoglobin saturation. It is well known that oxyhemoglobin is redder than deoxyhemoglobin. As such, deoxyhemoglobin nominally absorbs light at 603 nm more intensely than oxyhemoglobin. There is another difference in absorption characteristics of these two species which is not visible: oxyhemoglobin nominally absorbs light at 940 nm more intensely than deoxyhemoglobin. The quantity of light absorbed at these two wavelengths is characteristic of a particular mix of oxy and deoxyhemoglobin. Hemoglobin saturation is calculated using absorbance data and a prediction curve which is generated by a large population study which correlates pulse oximetric data with traditional hemoglobin saturation measurements.

Tissue contains absorbing substances other than the species of hemoglobins. However, generally a pulse oximeter can isolate the absorbances of the hemoglobin species of interest from the absorbances of potentially interfering species. It does so by determining the difference between the absorbance of light by tissue before an arterial pulse and the absorbance of light by tissue at the peak of an arterial pulse. The difference in absorbance is attributed to arterial blood at the site of the measurement. In summary, the absorbance prior to a pulse is subtracted from the absorbance at the peak of a pulse to determine the percentage oxygen saturation of arterial blood hemoglobin.

U.S. Pat. No. 4,819,752, the disclosure of which is incorporated herein by reference, discloses a pulse oximeter type device which measures hemoglobin saturation using these principles. The device disclosed in this patent differs from prior an methods in the way in which it processes signals, in relation to isolating the pulsatile component, determining the size of the pulsatile component and in determining the size of the non-pulsatile component.

Similarly, U.S. Pat. No. 4,805,623, the disclosure of which is incorporated herein by reference, describes a spectrophotometric method of measuring the concentration of a dilute component such as hemoglobin in a light- or other radiation scattering environment. The disclosed crux of the invention involves simultaneous measurement of the absorbed/reflected light of the dilute and of the reference components. Essential features of the method employed in U.S. Pat. No. 4,805,623 include, determination of path-length and an extinction coefficient of the analyte in the light-scattering environment, along with use of complex theoretical formulas.

As is generally known to those of ordinary skill in the art, in-vivo spectrophotometric measurements are complicated by scattering losses, difficulties in path-length measurement and spectroscopic interference from species other than those of interest. Spectrophotometric analysis is typically based on a model that assumes pure collimated light is reduced in intensity only by absorbing species. The intensity is reduced by an exponential process known as "Beer's law", wherein absorbance is proportional to concentration. A classical Beer's law approach to analyte measurement in tissue, using a path-length and extinction coefficient determination however, generally gives clinically unacceptable results due at least in part to the complications referred to above.

The method of the present invention differs fundamentally from that of U.S. Pat. No. 4,805,623 ("the '623 patent") in that it does not require a light path-length or an extinction coefficient determination. Furthermore, in a preferred embodiment the method of the present invention employs a pulse based measurement by using a pulse oximeter which has been modified to make measurements at the appropriate wavelengths for hemoglobin concentration.

Spectrophotometric methods have also been utilized to measure hemoglobin concentration in-vitro. These methods are generally referred to using the terminology "in-vitro hemoglobinometry". In the most commonly used method of in-vitro hemoglobinometry, a blood sample is diluted, lysed and treated with potassium cyanide. An absorbance reading is taken at 540 nm and compared with that of a standard solution. This method is described in *Clinical Diagnosis & Management By Laboratory Methods*, Henry, John B. (W. B. Saunders Company, Philadelphia, 18 1h Ed. 1991).

SUMMARY OF THE INVENTION

The method of the present invention comprises scanning tissue, in-vive, or a blood sample, in-vitro, with a plurality of wavelengths of light in the visible and near-infrared region including analyte wavelengths and reference wavelengths. The absorbance data is combined in ratio form which minimizes and preferably eliminates the need to calculate a path-length and an extinction coefficient and the need to estimate unpredictable scattering losses.

In the in-vive setting, a pulse oximeter, which has been appropriately modified include wavelengths for hemoglobin concentration, may be employed in order to isolate the absorbance of blood from the absorbance due to tissue other than blood. Specifically, multiple light emitting diodes are used which are of the appropriate wavelengths for hemoglobin concentration measurement. Hemoglobin concentration is obtained by comparing spectral data to prediction table data which have been obtained with correlation studies.

In particular embodiments of the present invention, multiple light emitting diodes may be utilized to emit light at a sufficient number of wavelengths to generate derivative spectral data or, alternatively, to emit light at multiple wavelengths which provide a hemoglobin concentration using ordinary absorbance dam. In either case, the light emitting diodes would preferably be utilized with a modified pulse oximeter to obtain a pulse based measurement.

Alteratively, hemoglobin measurements could be made in the in-vive and in the in-vitro settings using derivative (with respect to wavelength) spectroscopy without the need for a pulse oximeter. For example, using second derivative spectroscopy, hemoglobin measurements can be made using ratios of derivative data with a conventional spectrometer.

The present invention advantageously provides a method for non-invasive hemoglobin measurement. This method has a variety of potential uses. For example, prior to accepting blood donations, blood collection centers must immediately determine that a potential donor is not anemic. Currently, this determination is done by pricking a donor's finger and extracting a drop of blood. Pediatric clinics also frequently use the finger stick method for rapid hemoglobin concentration. This method disadvantageously exposes the potential donor to minor pain and results in the possibility of blood-borne infection patient and technical personnel. It would be desirable to offer a painless non-invasive measurement in the above settings.

In addition it has become state of the an in intensive care units and in operating rooms to monitor hemoglobin saturation with the pulse oximeter. The present invention could be incorporated in the current pulse oximeter with relative ease and would offer additional clinically relevant information.

The present invention also advantageously provides a method for in-vitro hemoglobin measurement, which may be performed on a whole blood sample and minimizes, or eliminates, the need for reagents or for lysis of the blood. In addition, there is no release of harmful reagents such as cyanide into the environment. The in-vitro method of the present invention comprises scanning a blood sample, in-vitro, with a plurality of wavelengths of light in the visible and near-infrared region including analyte wavelengths and reference wavelengths. Preferably, a vertical light path is used in scanning. The absorbance data is combined in ratio form which minimizes and preferably eliminates the need to calculate a path-length and an extinction coefficient and the need to estimate unpredictable scattering losses. The in-vitro method of hemoglobin measurement of the present invention could be incorporated into large laboratory based hematology analysers or into hand held devices for hemoglobin concentration measurement.

BRIEF DESCRIPTION OF THE DRAWINGS

FIG. 9 depicts a second derivative spectrum of unlysed blood.

DETAILED DESCRIPTION

While performing spectroscopic studies on human tissue, it was noted that capillary bed tissue has a visible light spectrum which resembles that of hemoglobin. It was also noted that this same tissue has a near-infrared spectrum which is similar to that of water This observation forms the basis of a hemoglobin concentration measurement.

The essence of any concentration measurement is comparison of at least two components. In the usual in-vitro hemoglobin measurement, the absorbance of a blood sample of unknown concentration is compared to a reference curve which is generated using samples of known concentration. In tissue, similar information can be obtained by using a reference which is the absorbance of the tissue at a wavelength other than the hemoglobin absorption band which is referred to as the analyte wavelength. This reference absorbance provides a guage by which one can measure the size of the hemoglobin absorption band, i.e., the hemoglobin concentration.

Figure 1:
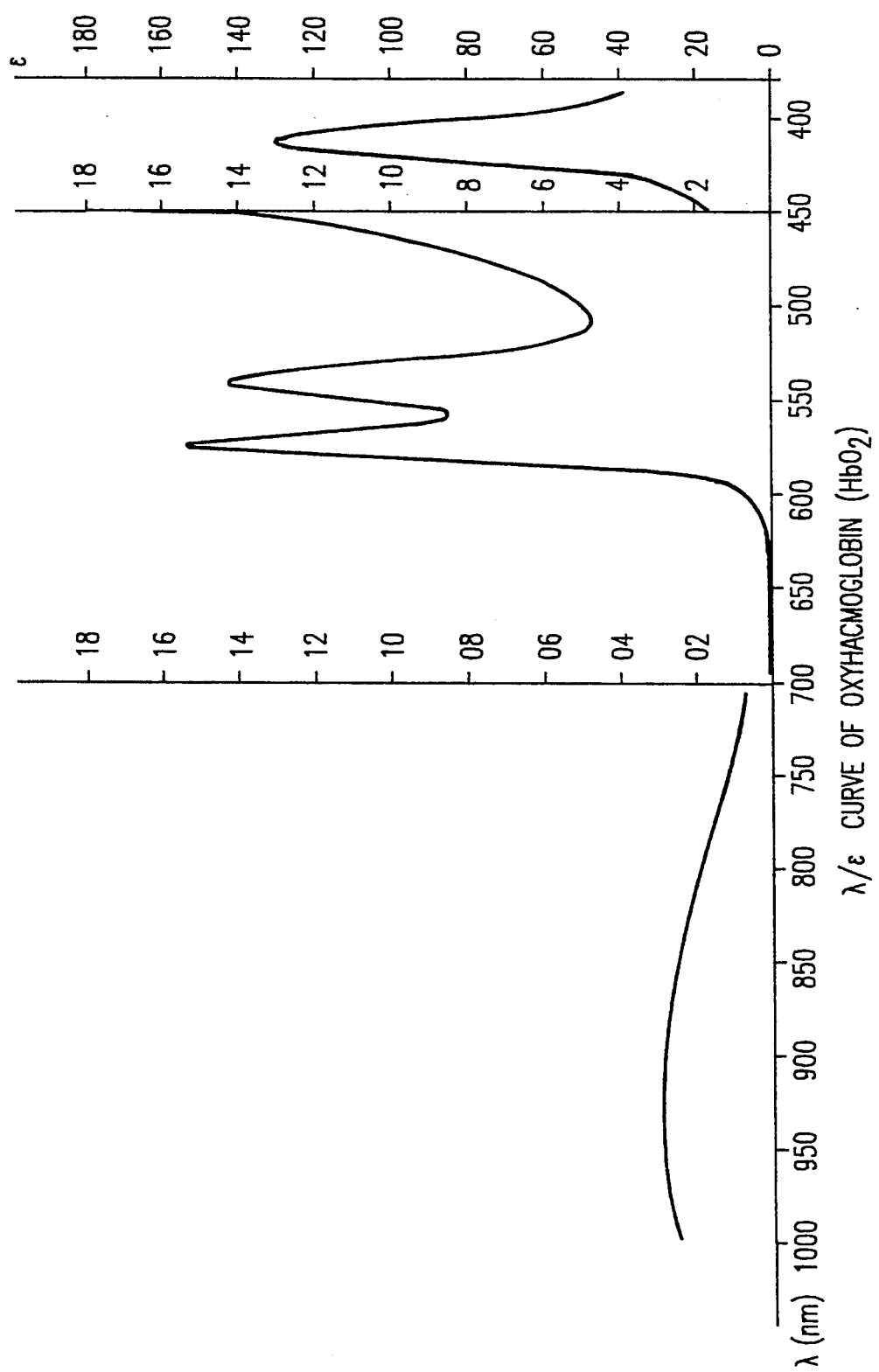
FIG. 1 is a visible light spectrum of oxyhemoglobin.
Figure 2:
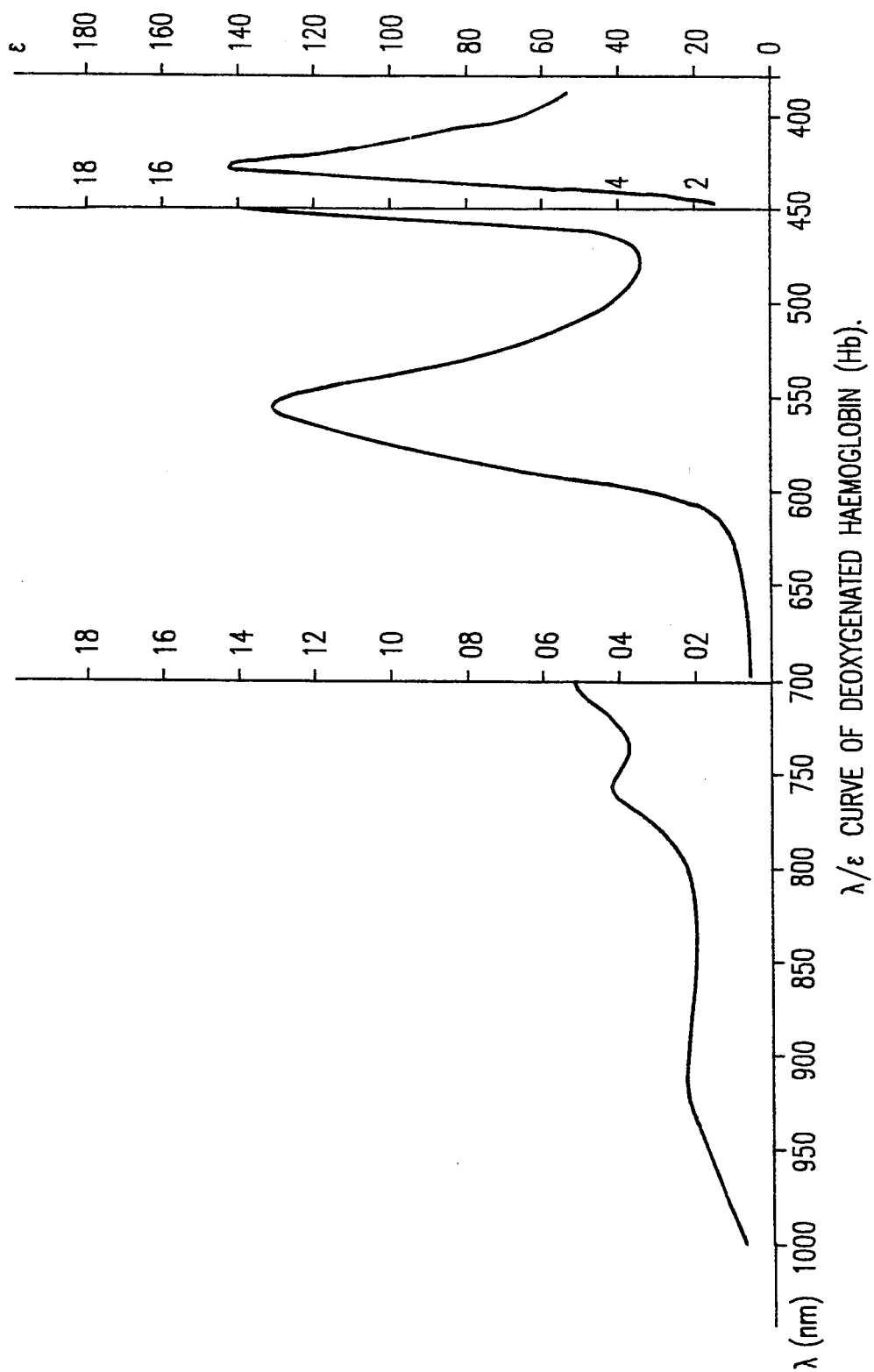
FIG. 2 is a visible light spectrum of deoxyhemoglobin.
Figure 3:
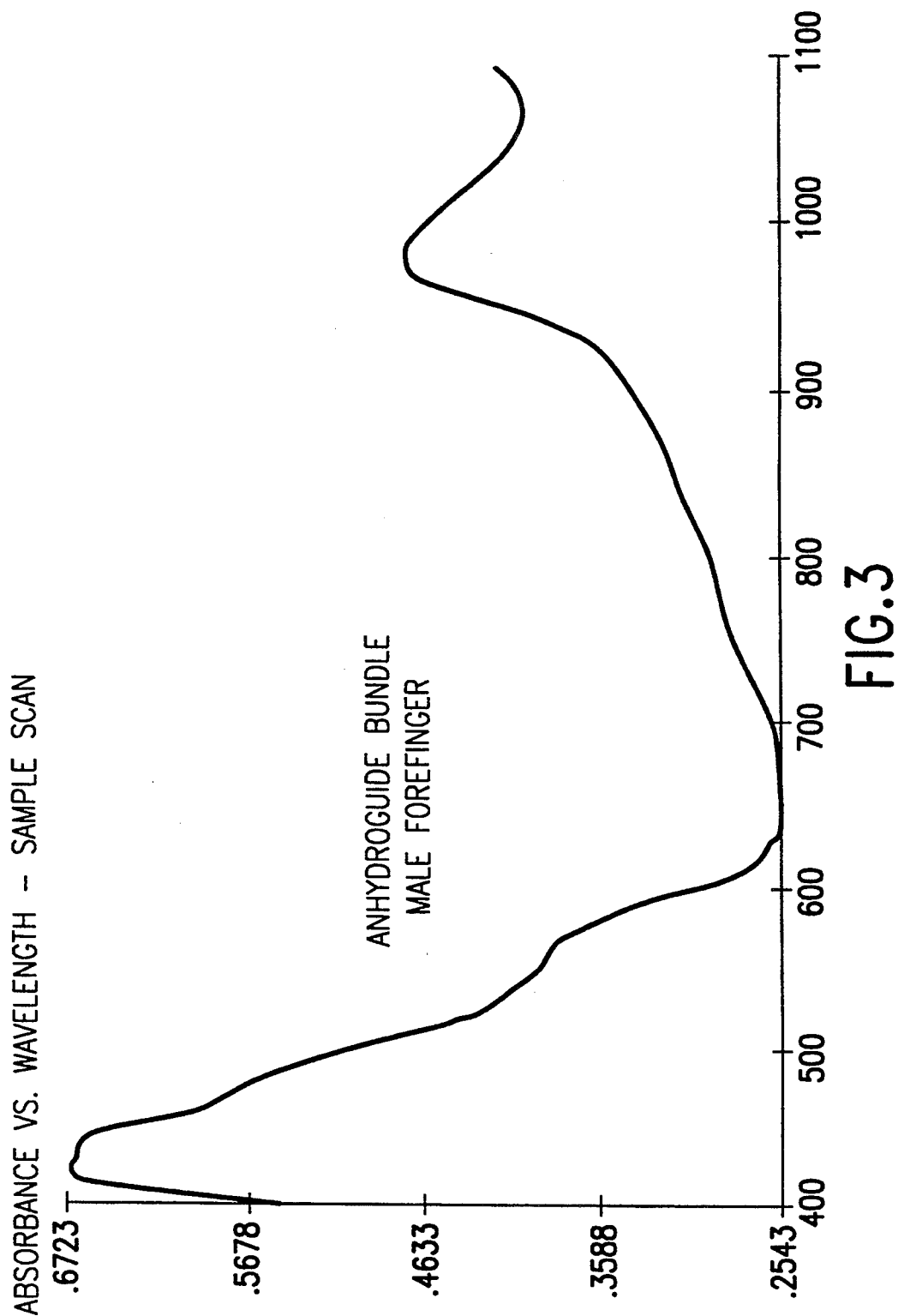
FIG. 3 is a visible light spectrum of a finger of the inventor using the reflectance mode.

FIGS. 1 and 2 are visible light spectra of the species of hemoglobin. As seen in these spectra, the absorbance of both species of hemoglobin reaches the highest amplitude in the region from 400 to 450 nm. The similarity to the visible light spectrum in FIG. 3 should be noted. The visible light spectrum of capillary bed tissue of the finger is similar to a combination spectrum of the two species of hemoglobin.

Figure 5:
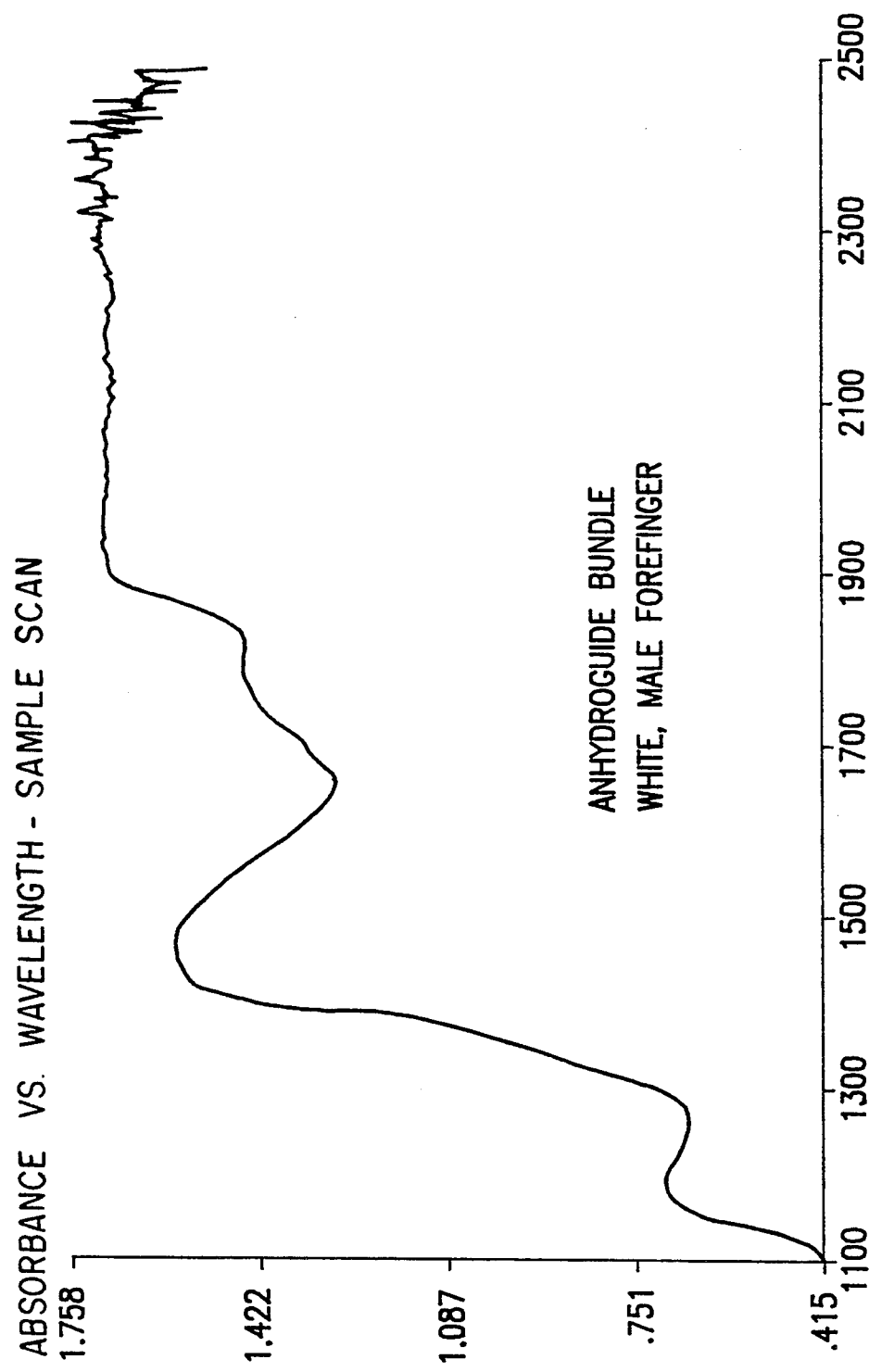
FIG. 5 is a near-infrared spectrum of a finger of the inventor using the reflectance mode.
Figure 6:
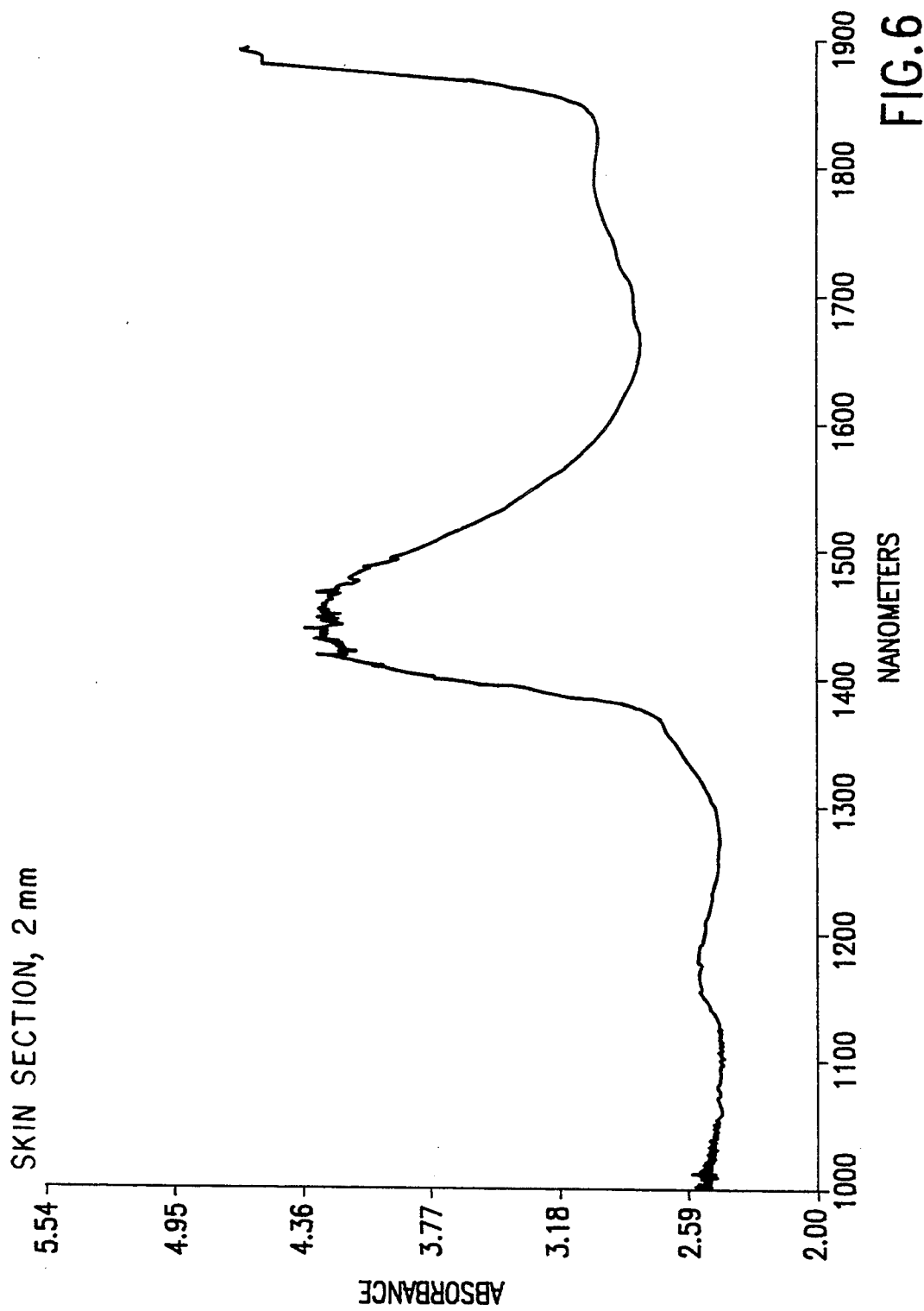
FIG. 6 is a near-infrared spectrum of cadaveric skin using the transmittance mode.

FIG. 4 shows the near-infrared spectrum of water. Absorption bands are seen at approximately 940 nm, 1140 nm and 1460 nm. There is a trough at approximately 1370 nm. FIGS. 5 and 6 show near-infrared spectra of human tissue in the reflectance and transmittance modes, respectively. Likewise, there is a similarity between the near-infrared spectrum of water and of tissue. In tissue, absorption bands are also seen at approximately 940 nm, 1140 nm and 1470 nm and a trough is seen at approximately 1370 nm. This similarity makes sense when one considers the fact that capillary bed tissue is approximately 80 to 90% water.

In the earliest work done by this inventor, a single term ratio of two absorbances in the near-infrared region was used to measure hemoglobin concentration in unlysed blood samples. An analyte wavelength of 816 nm, which is an isobestic point in the spectra of the major hemoglobin species, i.e., oxy and deoxyhemoglobin, and a reference wavelength of 1370 nm were used. A weak correlation with the traditional hemoglobin concentration was observed using this approach. Improved results were obtained when using single-term ratios of derivative (with respect to wavelength) spectral data to measure hemoglobin concentration in unlysed blood samples. For example, using a single-term ratio of second derivative log (1/T) data at 1740 and 1346 nm, hemoglobin concentration could measured with a standard error of 0.43 g/dL and an $R^2$ of 0.986. In fact, there are numerous areas in the near-infrared region in which accurate measurement of hemoglobin is possible using single-term ratios of derivative absorbance data. A more detailed description of my earlier work in hemoglobin measurement is found in my earlier patent applications, Ser. No. 07/965,817, filed Oct. 23, 1992 and Ser. No. 7/880,379, filed May 8, 1992. The disclosure of each of these applications is hereby incorporated herein by reference.

A summary of representative regions from which analyte/reference wavelength combinations can be selected and of a few particularly suitable wavelength combinations appears below. This list is by no means exhaustive.

| Analyte Wavelength | Reference Wavelength | Derivative |
|---|---|---|
| 1735–1749 nm | 1669–1679 nm | second |
| 1744 nm | 1674 nm | second |
| 1740 nm | 1346 nm | second |
| 2203–2213 nm | 2177–2187 nm | first |
| 2208 nm | 2182 nm | first. |

In the second derivative spectrum of hemoglobin, other analyte regions useful for hemoglobin measurement include the bands which are centered at 1694 nm, 20.54 nm and nm.

While one may accurately measure hemoglobin concentration in unlysed blood samples using derivative spectroscopy, there are other methods of measurement which may also be useful in an in vivo and/or in vitro setting.

For this reason, an additional approach was devised which uses absorbance data at multiple wavelengths combined in a ratio which eliminates the need for a path-length measurement and compensates for unpredictable scattering losses. A device using either derivative or ordinary absorbance data could use light emitting diodes at the appropriate wavelengths and could be used with a modified pulse oximeter which is operated in either the transmittance or the reflectance mode. In this fashion, it is anticipated that absorbance due to hemoglobin can be isolated from the absorbance due to tissue proteins. In order to determine hemoglobin concentration a microprocessor is programmed to receive the absorbance data and to calculate the hemoglobin concentration according to a previously generated prediction table formed with correlation studies.

It was found that the above approach using absorbance data at multiple wavelengths combined in a ratio which eliminates the need for a path-length measurement and compensates for unpredictable scattering losses could be used to measure the hemoglobin content of unlysed blood samples. The results for the calibration set were a standard error of 0.386 g/dL and an R of 0.9931, and for the prediction set were a standard error of 0.384 g/dL and an R of 0.9911. The calibration equation with which this data was obtained had the form:

$$H = b_0 + b_1 X_1(W_1) + b_x X_2(W_2) + b_3 X_3(W_3) + \ldots$$

where:
H is the hemoglobin concentration,
the subscripted b's are weighting factors, and
the subscripted X(W)'s are the absorbance data at wavelength W.

The set of wavelengths and weighting factors which yielded the above prediction characteristics is summarized below. As a means to normalize the data, this calibration divides the absorbance at each of the following wavelengths by the absorbance at 1450 nm. However, this set of wavelengths and weighting factors is not the only set which will predict hemoglobin content accurately, and the method of the present invention is not limited to use with these wavelengths.

| Wavelength (nm) | b |
|---|---|
| $b_o$ | −25.71 |
| 676 | 29.62 |
| 1116 | 1291.71 |
| 1132 | −1307.16 |
| 2100 | 25.09 |
| 1450 | normalization factor used as a divisor. |

As will be recognized by those of ordinary skill in the art, the methods of the present invention may also be utilized to measure the concentration of other substances in the blood including, but not limited to, urea, glucose and cholesterol. For example, in order to measure the concentration of cholesterol in the blood a ratio may be formed by scanning tissue, in-vivo, or a blood sample, in-vitro, with a plurality of wavelengths of light and dividing a sum of ordinary absorbances of cholesterol at a plurality of near-infrared and/or mid-infrared wavelengths, by absorbance at a reference wavelength. An appropriately modified pulse oximeter may be utilized to perform these measurements. Thus, the method of the present invention includes a non-invasive method for measuring a substance in blood selected from the group consisting of urea, glucose and cholesterol using a measurement comprising a ratio formed by dividing a sum of ordinary absorbance at a plurality of near-infrared wavelengths, or a sum of ordinary absorbance at a plurality of mid-infrared wavelengths, by the absorbance at a reference wavelength.

Further details and advantages of the present invention will become apparent from the following examples.

EXAMPLE 1

Figure 7:
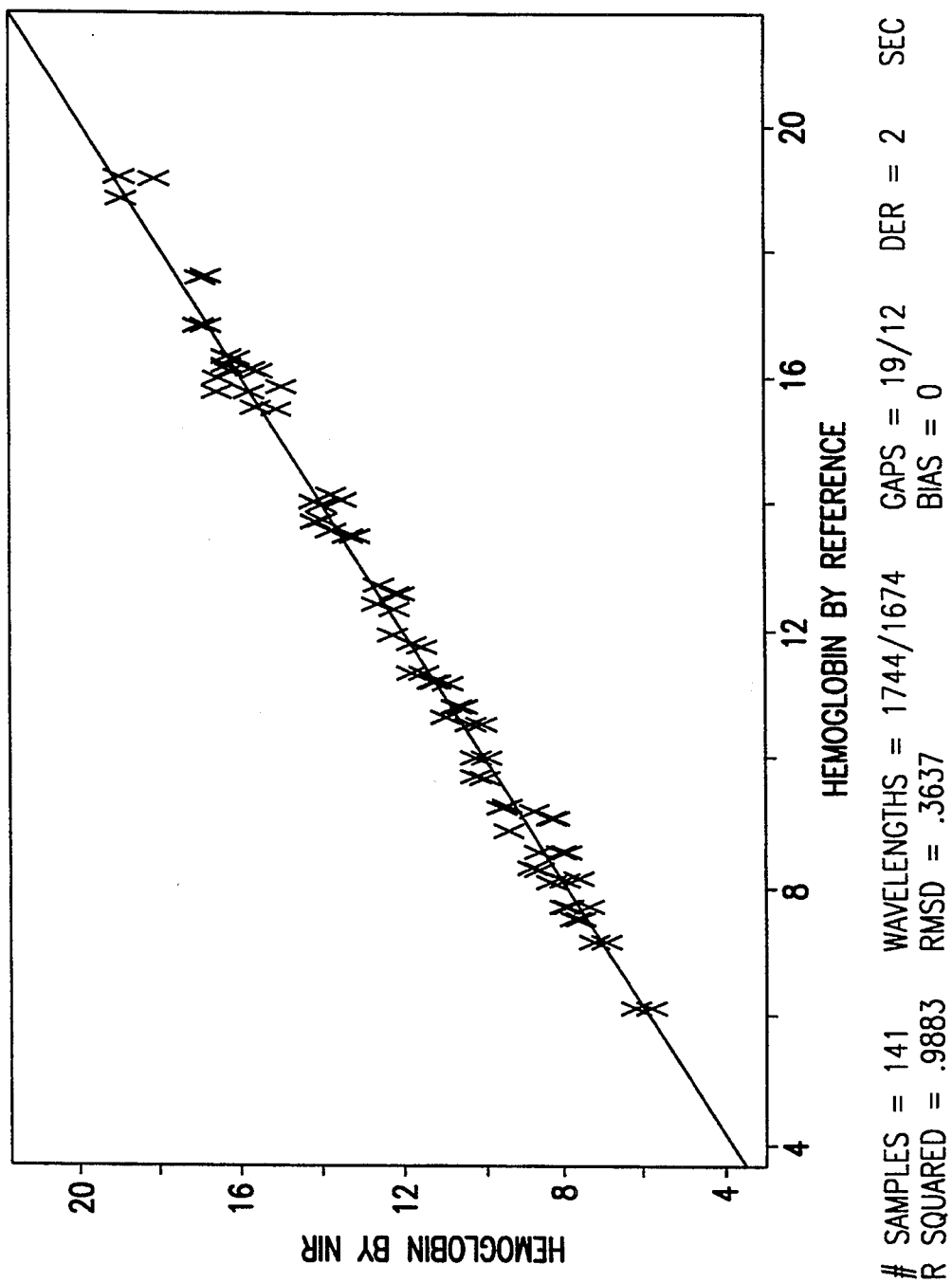
FIG. 7 is a correlation plot of the near-infrared spectroscopic measurement using ratios of derivative absorbance data versus the Coulter STKS monitor hemoglobin measurement.

A spectroscopic measurement of hemoglobin concentration in a large population of unlysed blood samples was sought. Visible and near-infrared transmittance (T) spectra of unlysed blood samples were obtained with an NIRSystems Model 6500 Spectrophotometer modified for an open cell and a vertical light path. The path length and temperature of the samples were not rigidly controlled. Hemoglobin content could be measured using a single-term ratio of second derivative (with respect to wavelength) log (1/T) data at 1740 nm and 1346 nm with a standard error of 0.43 g/dL and an $R^2$ of 0.986. Calibration was done on a set of 104 samples (2 spectra of blood from 52 patients) having hemoglobin levels of 6.1 to 19.2 g/dL. Validation was done on an independent set of 56 samples (2 spectra of blood from 28 patients) having hemoglobin levels of 7.2 to 19.0 g/dL. The reproducibility of the measurement, tested by computing the coefficient of variability of the 28 duplicated results, was 0.63%. Evidence that other near-infrared regions can be used for hemoglobin measurement as well was obtained. As shown in FIG. 7, an $R^2$ of 0.9:88 was obtained when the wavelength pair used for the measurement was 1744 nm and 1674 nm.

EXAMPLE 2

Figure 8:
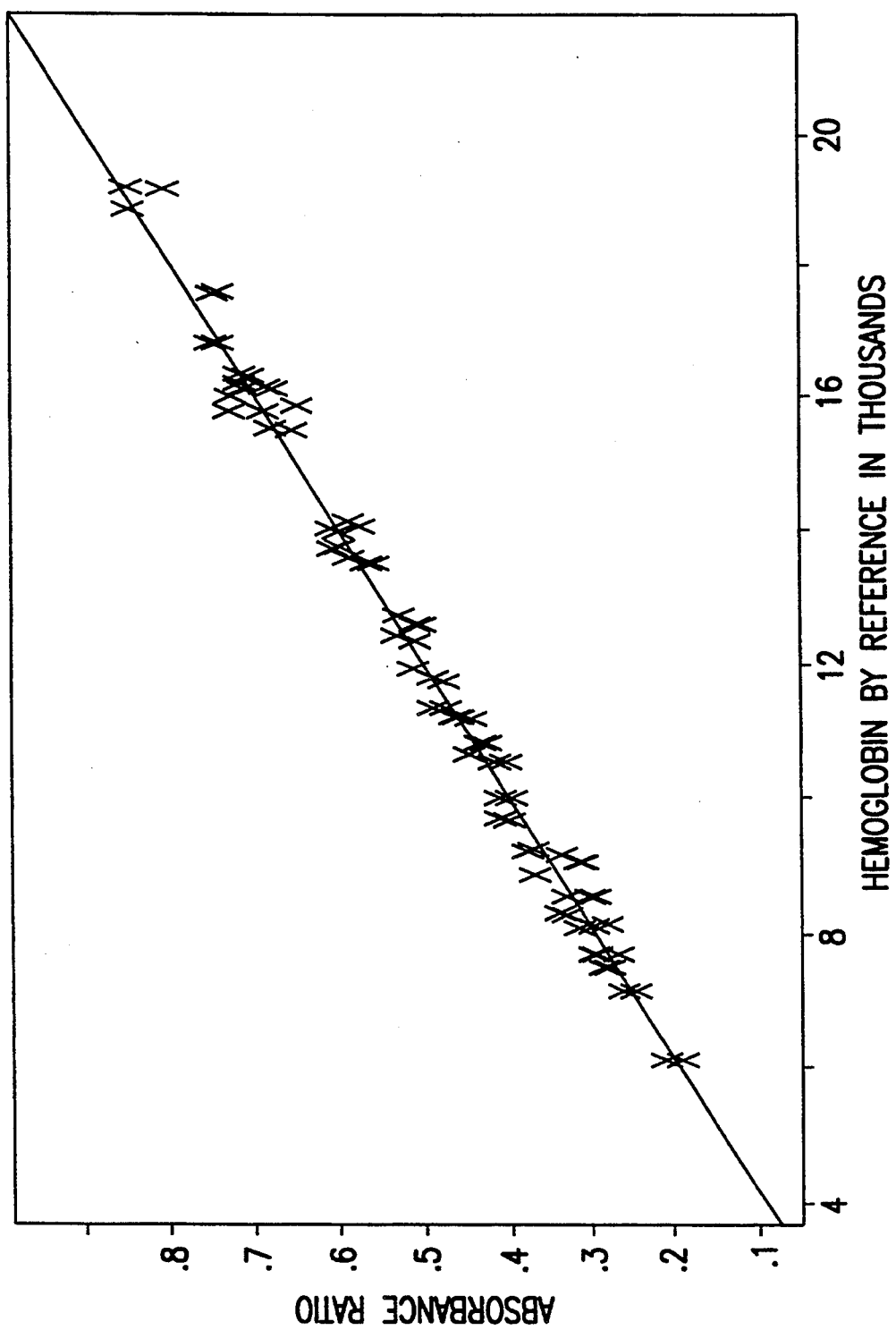
FIG. 8 depicts a hypothethical reference curve.

This example illustrates the use of one of the in-vitro methods of the present invention to determine a patient's hemoglobin level. Using the procedure set forth in Example 1, a reference curve can be generated by graphing a ratio of derivative absorbance data for each patient versus the hemoglobin concentration by a reference method such as the Coulter STKS Monitor. A hypothetical reference curve is shown in FIG. 8.

An infrared spectrophotometer is used to shine light vertically through an unlysed blood sample. A derivative transformation (with respect to wavelength) of the spectral data is carded out and an appropriate single-term ratio of derivative absorbance data is used the measurement.

FIG. 9 depicts the resulting second derivative absorbance spectrum of a representative unlysed blood sample. From inspection, the second derivative of absorbance at an analyte wavelength of 1744 nm divided by the second derivative of absorbance at a reference wavelength of 1674 nm is yA/yR=3 mm/13 mm=0.23. From inspection of FIG. 8, which is the reference curve, when the ratio of second derivative absorbance data is 0.23, the patient's hemoglobin concentration is 6.6 g/dL. Using the measurement which consists of multiple wavelengths of absorbance data combined in ratio form, a similar process is used to obtain a patient's hemoglobin concentration.

As will be realized by those of ordinary skill in the art from the foregoing description, the method of the present invention presents a simple procedure for in-vitro and in-vivo determination of a patient's hemoglobin concentration.

I claim:

1. A non-invasive method for determining hemoglobin concentration comprising:
    generating an absorbance data measurement by
        measuring the absorbance of light at a plurality of wavelengths, including multiple analyte and multiple reference wavelengths, in the near-infrared and long wavelength visible regions, in capillary bed tissue during the peak of a blood pulsation through the tissue; and
        measuring the absorbance of the light at the plurality of wavelengths in capillary bed tissue during the trough of a blood pulsation through the tissue;
    and comparing the absorbance dam measurement to a reference curve which is generated by a correlation study to determine the hemoglobin concentration of the tissue.

2. The method of claim 1 wherein the measurement consists of ordinary absorbance data at multiple wavelengths and the method further comprises combining the ordinary absorbance data at multiple wavelengths in ratio form and comparing the ratio to the reference curve.

3. The method of claim 1 wherein the measurement consists of derivative absorbance data at multiple wavelengths and the method further comprises combining the derivative absorbance data at multiple wavelengths in ratio form and reference curve.

4. The method of claim 1 wherein the absorbance data measurement is obtained by use of light emitting diodes and a modified pulse oximeter which together substantially simultaneously emit light at the multiple wavelengths appropriate for hemoglobin at the peak and trough of a blood pulsation.

5. The method of claim 1 wherein the capillary bed tissue is from a monitoring site on a patient selected from the group consisting of the patient's finger, the patient's toe, the patient's ear lobe and the web space tissue of the patient's hand.

6. A method for determining hemoglobin concentration in a blood sample comprising:
    generating an absorbance data measurement by measuring the light at a plurality of wavelengths, including multiple analyte and multiple reference wavelengths, in the near-infrared and long wavelength visible regions, in a blood sample;
    and comparing the absorbance data measurement to a reference curve which is generated by a correlation study to determine the hemoglobin concentration of the sample.

7. The method of claim 7 wherein the measurement consists of ordinary absorbance data at multiple wavelengths and the method further comprises combining the ordinary absorbance data at multiple wavelengths in ratio form and comparing the ratio to the reference curve.

8. The method of claim 6 wherein the measurement consists of derivative absorbance data at multiple wavelengths and the method further comprises combining the derivative absorbance data at multiple wavelengths in ratio form and comparing the ratio to the reference curve.

9. The method of claim 6 wherein the measurement consists of a sum of absorbance data at multiple wavelengths with calibration factors for the absorbance at each wavelength and the method further comprises comparing the sum of absorbance data at multiple wavelengths to the reference curve.

10. The method of claim 6 wherein the sample is unlysed whole blood.

11. The method of claim 6 wherein the light used in the measurement traverses a vertical path.

* * * * *

UNITED STATES PATENT AND TRADEMARK OFFICE
CERTIFICATE OF CORRECTION

PATENT NO. : 5,377,674　　　　　　　　　　　　Page 1 of 3
DATED　　　: Jan. 3, 1995
INVENTOR(S) : J. Todd Kuenstner It is certified that error appears in the above-indentified patent and that said Letters Patent is hereby corrected as shown below:

On title page, item [76], change "kuestner"
　　　　　　　　to --Kuenstner--.

| Column | Line | |
|---|---|---|
| 2 | 1  | Change "prior an" to --prior art--. |
| 2 | 51 | Change "18lh" to --18th--. |
| 2 | 55 | Change "in-vive" to --in-vivo--. |
| 2 | 63 | Change "in-vive" to --in-vivo--. |
| 2 | 64 | After "modified" insert --to--. |
| 3 | 10 | Change "dam" to --data--. |
| 3 | 14 | Change "Alteratively" to --Alternatively--. |
| 3 | 15 | Change "in-vive" to --in-vivo--. |
| 3 | 29 | After "rapid" insert --determination of--. |
| 3 | 32 | After "infection" insert --of--. |
| 3 | 35 | Change "an" to --art--. |

UNITED STATES PATENT AND TRADEMARK OFFICE
CERTIFICATE OF CORRECTION

Figure 4A:
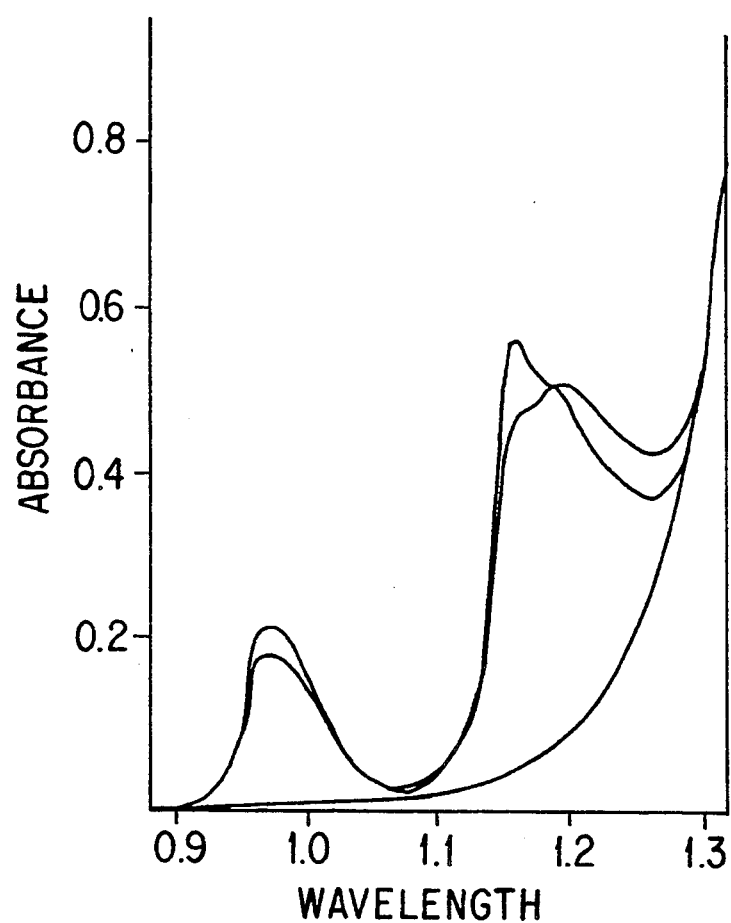
FIG. 4 is a near-infrared spectrum of water.

PATENT NO.  : 5,377,674                     Page 2 of 3
DATED       : Jan. 3, 1995
INVENTOR(S) : J. Todd Kuenstner It is certified that error appears in the above-indentified patent and that said Letters Patent is hereby corrected as shown below:

| Column | Line | |
|---|---|---|
| 3 | 68 | Change "FIG. 4 is a" to --FIGS. 4 and 4A are--. |
| 4 | 18 | After "water" insert --.--. |
| 4 | 42 | Change ""FIG. 4 shows" to --FIGS. 4 and 4A show--; change "spectrum" to --spectra--. |
| 4 | 68 | After "could" insert --be--. |
| 5 | 25 | Change "20.54" to --2054--. |
| 5 | 26 | After "and" insert --2170--. |
| 5 | 54 | Change "R" to --$R^2$--. |
| 5 | 56 | Change "R" to --$R^2$--. |
| 5 | 59 | Change "...$b_x$..." to --...$b^2$...--. |

UNITED STATES PATENT AND TRADEMARK OFFICE
CERTIFICATE OF CORRECTION

PATENT NO. : 5,377,674
DATED : Jan. 3, 1995
INVENTOR(S) : J. Todd Kuenstner

It is certified that error appears in the above-indentified patent and that said Letters Patent is hereby corrected as shown below:

| Column | Line | |
|---|---|---|
| 6 | 63 | Change "0.9:88" to --0.988--. |
| 7 | 10 | Change "carded" to --carried--. |
| 7 | 45 | Change "dam" to --data--. |
| 8 | 7 | Before "reference" insert --comparing the ratio to the--. |
| 8 | 22 | Before "light" insert --absorbance of--. |
| 8 | 30 | Change "claim 7" to --claim 6--. |

Signed and Sealed this

Twenty-ninth Day of August, 1995

Attest:

BRUCE LEHMAN

*Attesting Officer*  *Commissioner of Patents and Trademarks*